(12) United States Patent
O'Day

(10) Patent No.: US 8,012,122 B2
(45) Date of Patent: Sep. 6, 2011

(54) ELONGATED MEDICAL APPARATUS WITH INFLATABLE TIP

(75) Inventor: Therese J. O'Day, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 51 days.

(21) Appl. No.: 12/039,158

(22) Filed: Feb. 28, 2008

(65) Prior Publication Data
US 2009/0221959 A1    Sep. 3, 2009

(51) Int. Cl.
*A61M 29/00* (2006.01)

(52) U.S. Cl. .................. 604/102.03; 604/96.01

(58) Field of Classification Search ........... 604/96.01, 604/101.03, 101.04, 101.05, 102.01, 102.02, 604/102.03, 103.01, 103.02; 606/192, 194; 623/1.11
See application file for complete search history.

(56) References Cited

U.S. PATENT DOCUMENTS

| | | | |
|---|---|---|---|
| 4,022,216 A * | 5/1977 | Stevens | 604/101.03 |
| 4,714,460 A * | 12/1987 | Calderon | 604/28 |
| 4,913,139 A | 4/1990 | Ballew | 128/200.11 |
| 5,318,586 A | 6/1994 | Ereren | 606/192 |
| 5,749,357 A | 5/1998 | Linder | 128/200.26 |
| 5,795,332 A * | 8/1998 | Lucas et al. | 604/103 |
| 6,689,097 B2 * | 2/2004 | Thramann | 604/96.01 |
| 2002/0165486 A1 * | 11/2002 | Bertolero et al. | 604/102.01 |
| 2006/0081260 A1 | 4/2006 | Eells et al. | 128/207.29 |
| 2007/0173785 A1 * | 7/2007 | Ostroot | 604/509 |

* cited by examiner

*Primary Examiner* — Christopher D Koharski
(74) *Attorney, Agent, or Firm* — Brinks Hofer Gilson & Lione

(57) ABSTRACT

An elongated medical apparatus suitable for insertion into a bodily passageway of a patient for carrying out a medical procedure. The elongated apparatus includes an elongated tubular body having a proximal portion and a distal portion, wherein the distal portion terminates at a distal end. The tubular body has a plurality of lumens extending therein. An inflatable balloon member is mounted at the distal end of the tubular body and extends in a distal direction therefrom. The balloon member is inflated by receiving an inflation fluid through one of the lumens. The presence of the balloon member at the leading end of the elongated apparatus reduces the risk of puncture and trauma upon insertion of the apparatus into the bodily passageway.

13 Claims, 2 Drawing Sheets

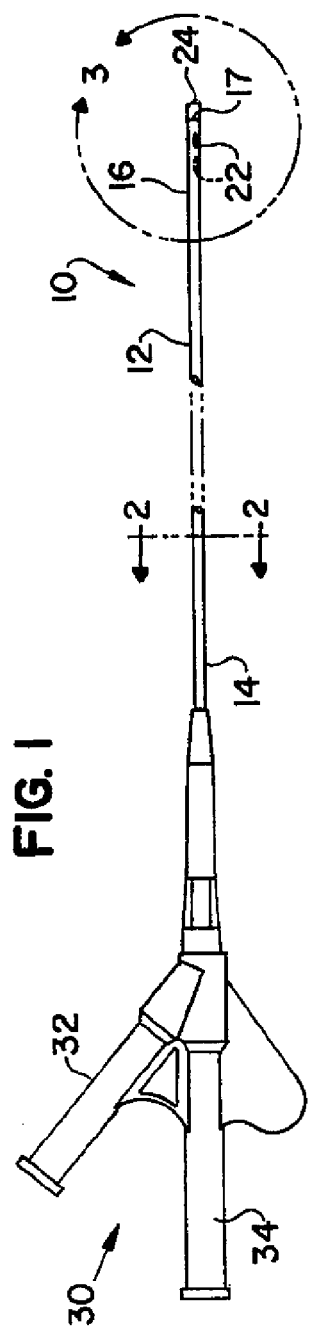
FIG. 1
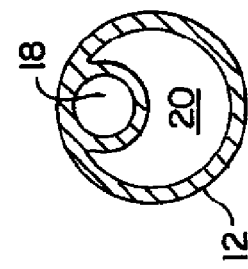
FIG. 2
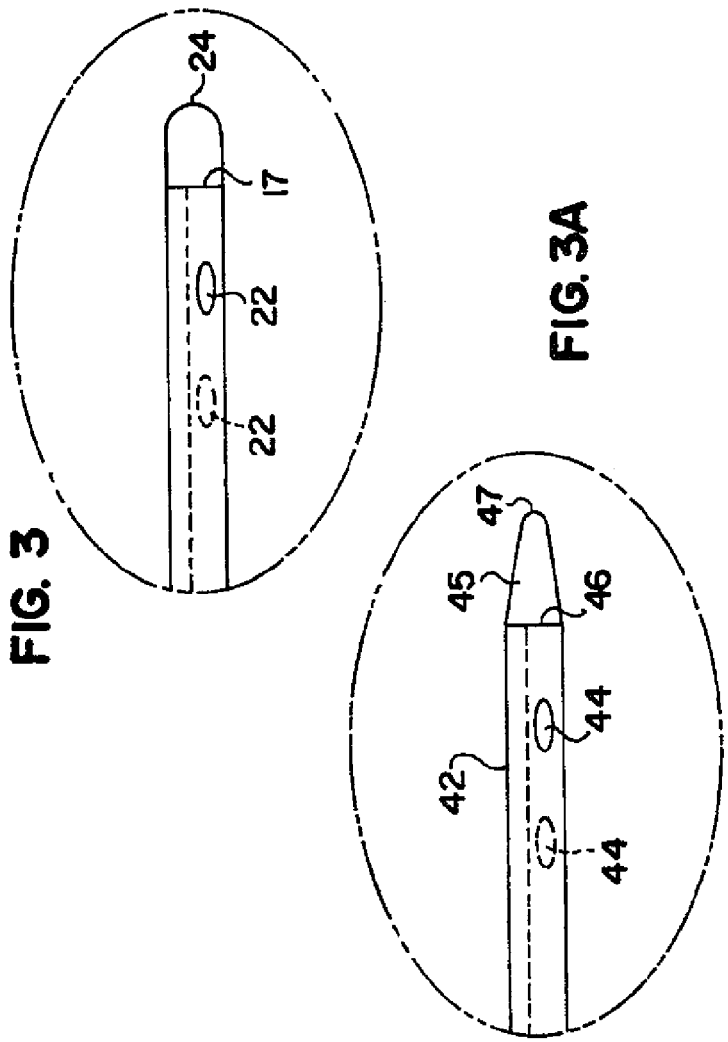
FIG. 3
FIG. 3A

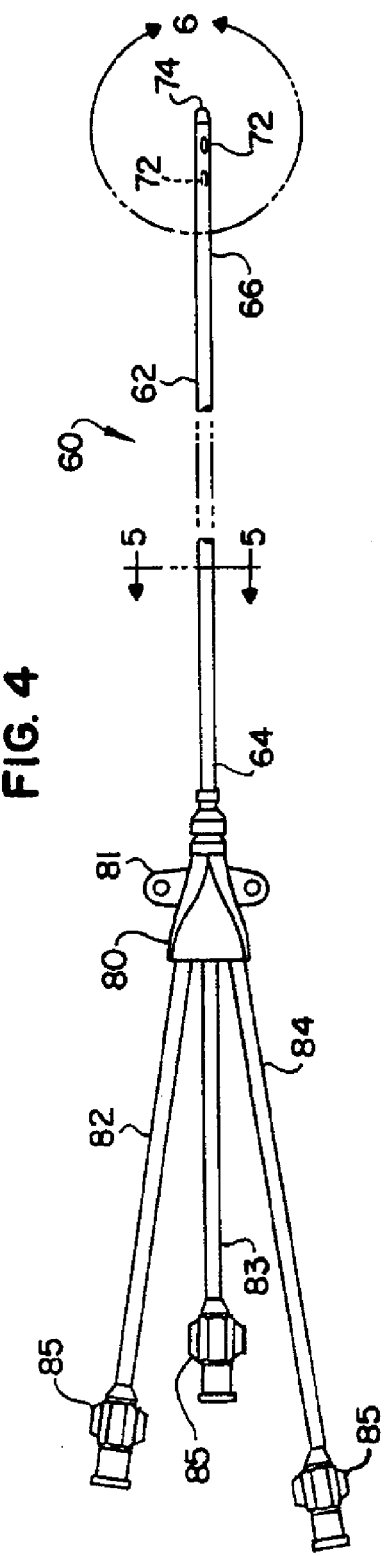
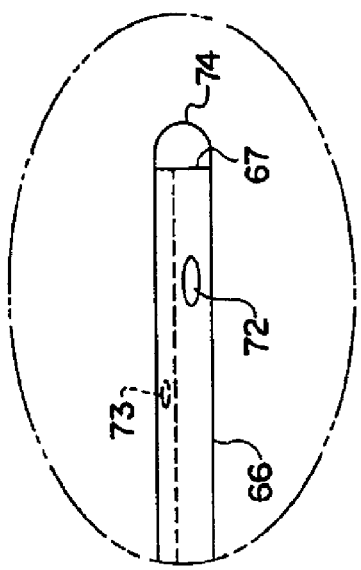
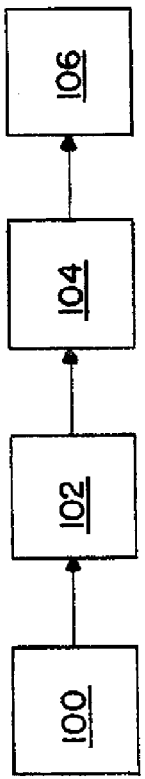
FIG. 4
FIG. 5
FIG. 5A
FIG. 6
FIG. 7

ELONGATED MEDICAL APPARATUS WITH INFLATABLE TIP

BACKGROUND

1. Technical Field

The present invention relates to a medical apparatus, and more particularly, to an elongated tubular apparatus having an inflatable leading end.

2. Background Information

Many innovative techniques in modern medicine involve the insertion of a medical device, such as a catheter or other elongated tubular apparatus, into remote sites within the body of a patient. Among others, such techniques include balloon angioplasty, the delivery of medical interventional devices and/or fluids to or from a target site, the introduction of nutritional materials to remote internal sites, and the introduction of fluids for use in diagnostic or other medical imaging techniques. The foregoing list represents only a small sampling of the types of medical techniques that have now become commonplace. Numerous additional techniques continue to be developed, and such development is expected to continue at a rapid pace in future years.

In many cases, the catheter or other elongated apparatus utilized in the medical technique must traverse tortuous passageways in the body to arrive at the intended destination. Ideally, such an apparatus will have sufficient rigidity to optimize the trackability of the apparatus, and yet not be so rigid as to prevent the apparatus from traversing the curves and bends encountered along the passageway. In addition, the apparatus would ideally have a leading (distal) end that is formed in a manner to reduce the risk of puncture and/or other trauma with sensitive tissue encountered by that end as the apparatus traverses the passageway.

The medical community has attempted to confront these concerns in many different ways. For example, some apparatuses are constructed from materials that provide the apparatus with a more rigid, or higher durometer, proximal end, and a less rigid, or lower durometer, distal end. Providing an apparatus having less rigidity at the distal end enables the leading end of the apparatus to more easily flex around the tortuous bends, while at the same time maintaining the trackability of the apparatus at the proximal end. Nevertheless, the distal end of such apparatuses must typically retain a sufficient amount of rigidity to enable it to track the particular target area. Other apparatuses incorporate a reinforcement, such as a helical coil, into the body of the apparatus that enables the apparatus to flex when necessary, and return to its original configuration without kinking following the flexure. Although such apparatuses exhibit a desirable amount of kink resistance in many instances, the leading end of the apparatus must still be capable of tracking the target area in a substantially non-traumatic manner.

These and related apparatuses have significantly improved the ability of the medical professional to introduce medical interventional devices, such as stents, and/or fluids to remote areas that had previously been difficult, if not impossible, to reach. However, passage of the apparatus to such remote areas exposes sensitive areas of the body to an apparatus that, in most cases, has a leading end that is still harder and more rigid than the tissue that it confronts along the passageway. In addition, the leading end of the apparatus also typically has a configuration that exposes the tissue to an increased risk of puncture and trauma.

It is desired to provide an elongated medical apparatus suitable for introduction into remote and sensitive areas of the body, wherein the elongated apparatus has a leading end that exhibits a reduced risk of puncture and/or trauma of the surrounding tissue when compared to existing apparatuses. It is also desired to provide a method for gaining access to body anatomy through a bodily passageway of a patient utilizing an elongated medical apparatus having an inflatable distal end.

BRIEF SUMMARY

The foregoing problems are addressed by the features of the present invention. In one form thereof, the present invention comprises an elongated medical apparatus suitable for insertion into a bodily passageway of a patient for carrying out a medical procedure. The apparatus comprises an elongated tubular body having a proximal portion and a distal portion, wherein the distal portion terminates at a distal end. The tubular body has a plurality of lumens extending therein. An inflatable member is mounted at the distal end of the tubular body and extends distally therefrom. An interior space of the inflatable member communicates with one of the lumens for receiving an inflation fluid therethrough.

In another form thereof, the present invention comprises a method for gaining access to body anatomy through a bodily passageway of a patient. An elongated medical apparatus comprising an elongated tubular body having a proximal portion and a distal portion is provided. The distal portion of the tubular body terminates at a distal end, and the tubular body has a plurality of lumens extending therein. An inflatable member is mounted at the distal end of the tubular body, and extends distally therefrom. The interior space of the inflatable member is in communication with a first one of the lumens for receiving an inflation fluid therethrough. An inflation fluid is passed through the first lumen into the interior space of the inflatable member to achieve at least partial inflation. The distal end of the elongated tubular body is inserted into the bodily passageway, and at least the distal end of said the tubular body is advanced to the targeted body anatomy.

BRIEF DESCRIPTION OF THE DRAWINGS

FIG. 1 is a side elevational view of a catheter having an inflatable tip according to an embodiment of the present invention;

FIG. 2 is a cross-sectional view of the catheter of FIG. 1 taken along line 2-2;

FIG. 3 is an enlarged side view of the distal end portion of the catheter of FIG. 1;

FIG. 3A is an enlarged side view of an alternative embodiment of the distal end portion of the catheter of FIG. 1, illustrating a tapered tip;

FIG. 4 is a side elevational view of another embodiment of a catheter according to the present invention;

FIG. 5 is a cross-sectional view of the catheter of FIG. 4 taken along line 5-5;

FIG. 5A is a variation of FIG. 5 showing lumens having different diameters;

FIG. 6 is an enlarged side view of the distal end portion of the catheter of FIG. 4; and FIG. 7 is a view depicting the method of gaining access to body anatomy.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention relates to an elongated medical apparatus having an inflatable leading (distal) end. In the following discussion, the terms "proximal" and "distal" will be used to describe the opposing axial ends of the apparatus, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component) that is at the greatest distance from the operator, or that is initially inserted into the patient.

FIGS. 1-3 illustrate one embodiment of an elongated medical apparatus 10 of the present invention. Elongated medical apparatus 10 includes an elongated tubular body 12 having a proximal portion 14 and a distal portion 16. Distal portion 16 terminates in a distal end 17. Elongated tubular body 12 may comprise a catheter or other elongated tubular medical device of a type that may be introduced and maneuvered through a bodily passageway for use in carrying out a medical procedure. Elongated tubular body 12 may be formed of a conventional polymer commonly used for such purposes. A non-limiting list of suitable materials includes polyurethane, silicone, polyethylene, PVC, and latex. Those skilled in the art will appreciate that other conventional materials used for such purposes in the medical device art may be substituted.

Elongated tubular body 12 includes lumens 18, 20 extending therethrough. Lumens 18, 20 are best shown in FIG. 2. In the non-limiting embodiment shown, lumen 18 comprises a smaller diameter lumen and lumen 20 comprises a larger diameter lumen. Smaller diameter lumen 18 is open at distal end 17, whereas larger diameter lumen 20 is closed at the distal end. An inflatable member, such as balloon 24, is positioned at the distal end 17 of distal portion 16. The interior space of balloon 24 is in communication with the open distal end of smaller diameter lumen 18.

Elongated medical apparatus 10 includes a conventional hub at its proximal end, such as hub 30 shown in FIG. 1. Hub 30 includes portions 32, 34 that extend generally in a proximal direction from tubular body 12. Each one of extended portions 32, 34 communicates with a separate one of lumens 18, 20. In the embodiment shown, extended portion 32 communicates with smaller diameter lumen 18, while extended portion 34 communicates with larger diameter lumen 20. A proximal end of extended portion 32 is connected by conventional means to a source of inflation fluid (not shown) for transmission of an inflation fluid, such as air or saline, through smaller diameter lumen 18 to the interior space of balloon 24. Preferably, the fluid source includes a conventional valve member for regulating the transmission of fluid through the extended portion, and therefore, through smaller diameter lumen 18.

A proximal end of extended portion 34 may be connected, e.g., to a source of fluid for transmission through larger diameter lumen 20, and thereafter, through one or more side ports 22 along the length of the tubular body. One example of suitable side ports 22 is shown in FIG. 3. Side ports 22 may be provided in any number, geometrical configuration (e.g., circular, oval, etc.), and arrangement that may be suitable for a particular purpose. The use of side ports in elongated medical devices is well known in the art, and the skilled artisan is readily capable of optimizing the number, configuration, and arrangement of side ports for a particular purpose. Examples of fluids to be transmitted through extended portion 24 and lumen 20 may include, among others, diagnostic or nutritional fluids. As an alternative to the above-described transmission of fluids into the body from an external fluid source, the situation may be reversed. In this variation, extended portion 34 may be connected to a reservoir for receiving bodily fluids, such as blood, withdrawn from a bodily passageway, such as a blood vessel, through lumen 20 via side ports 22.

Balloon 24 is securely engaged at distal end 17 of distal portion 16 in any convenient, leak-free, and secure fashion. Non-limiting examples of suitable engagement techniques include adhesion and heat sealing. These techniques, and others, are well known in the medical device arts. Those skilled in the art can readily fashion other engagement techniques that may be appropriate for a particular purpose.

Preferably, balloon 24 is formed from a compliant material, such as polyurethane, silicone, polyethylene, PVC, or latex. Those skilled in the art will appreciate that other known thermoset, thermoplastic and rubber compounds commonly used for such purposes in the medical arts may be substituted. Those skilled in the art will also appreciate that forming the balloon from the same, or a similar, composition as that of the elongated tubular body is often advantageous, as it enhances the formation of a secure bond therebetween. Compliant materials give the balloon a softer feel, and are often used when it is desired to hold a device or balloon in place within a body passageway. Non-limiting examples of such uses include maintaining a tracheostomy tube in place within the esophagus, and maintaining a secure placement of a balloon within the bladder. In these, and other, uses of such balloons, the trauma to adjoining tissue is generally minimized when compared to the use of a balloon formed from a less soft composition. Those skilled in the art are well aware of the uses and capabilities of compliant balloons, and can readily fashion other suitable uses for such balloons.

Notwithstanding the preferred use of compliant balloons as described, the inventive elongated apparatus may alternatively be formed utilizing a balloon formed from a non-compliant composition. Non-compliant balloons are typically formed of nylon or polyethylene, although those skilled in the art will appreciate that other non-compliant materials may be substituted. Although non-compliant balloons may readily be formed to have a rounded leading (distal) end, they do not have the softness associated with the use of compliant balloons. As a result, use of non-compliant balloons is more likely to result in trauma to the adjoining tissue when compared to the use of a balloon formed from a softer, more compliant composition. Non-compliant balloons are typically utilized in procedures, such as angioplasty, in which a harder balloon is desired, e.g., to break down plaque, and/or to compress a material against a vessel wall.

Preferably, balloon 24 is inflatable to a desired length extending in the distal direction from the distal end 17 of elongated tubular body 12. When a compliant balloon is utilized, the desired length of the balloon may be varied by the operator by controlling the amount of inflation fluid transmitted to the interior space of the balloon via lumen 18. Typically the balloon will be inflated such that it extends between about 0.5 and 5 cm, and more preferably, about 1 cm beyond the distal end 17 of tubular body 12. Those skilled in the art will appreciate that the inflated length of the balloon may, in many cases, depend on the diameter of the elongated tubular body 12. Thus, for example, a balloon attached to the end of a, e.g., 24 French (8 mm) catheter will have a greater length than a balloon attached to the end of a, e.g., 4 French (1.35 mm) catheter in most instances.

In the embodiment of FIGS. 1-3, the outer diameter of balloon 24 upon inflation is substantially the same as the outer diameter of tubular body 12, and the balloon has a relatively blunt leading (distal) end. FIG. 3A illustrates an alternative embodiment of the inventive elongated tubular medical apparatus. Dual lumen tubular body 42 is similar to tubular body 12 in the embodiment of FIGS. 1-3, and includes one or more side ports 44 as shown. In this alternative embodiment, balloon 45 tapers from a larger diameter configuration at tubular body distal end 46 to a smaller diameter tip 47. A tapered distal tip as shown may be beneficial in tracking the elongated apparatus through a narrow body vessel.

In the embodiments of FIGS. 1-3 and 3A, the elongated tubular body illustrated therein has dual lumens. Although this configuration may be appropriate in many instances, other configurations may also be utilized, which configurations are also considered within the scope of the invention.

FIGS. 4-6 illustrate an alternative embodiment of an elongated medical apparatus 60. Elongated apparatus 60 comprises an elongated tubular body 62 having a proximal portion 64 and a distal portion 66. Distal portion 66 terminates in a distal end 67 as before. Balloon 74 is positioned at the distal end 67 of distal portion 66.

In this embodiment, elongated tubular body 62 includes three lumens 68, 69, 70 extending therethrough. Lumens 68 and 69 comprise smaller diameter lumens, and lumen 70 comprises a larger diameter lumen. One of lumens 68, 69, 70 is open at distal end 67 for transmission of the inflation fluid. Preferably, the lumen open at the distal end comprises one of the smaller diameter lumens 68, 69 (e.g., lumen 68). The remaining lumens (69, 70) are closed at the distal end.

A variation of this embodiment is shown in FIG. 5A. In this variation, the smaller diameter lumens 68A and 69A are of different diameter. This embodiment is otherwise similar to the embodiment of FIGS. 4-6. Typically, the smallest diameter lumen, in this case lumen 68A, will comprise the inflation lumen. The remaining lumens are available for other purposes, such as fluid flow. Although lumen 70A is the largest diameter lumen in the arrangement illustrated in FIG. 5A, lumens 69A and 70A can alternatively be of the same diameter.

Elongated tubular body 62 may have one or more side ports for establishing communication between the respective lumens and an environment external of apparatus 60 for transmitting fluids therethrough. In the embodiment shown (FIG. 6), side port 72 provides communication between larger diameter lumen 70 and the external environment, and side port 73 provides communication with smaller diameter lumen 69 and the external environment. Those skilled in the art will appreciate that tubular body 62 can be fashioned to have any number, configuration, and arrangement of side ports as before.

The elongated medical apparatus 60 of FIGS. 4-6 also includes an optional hub at the proximal end of the apparatus. In this non-limiting embodiment, the hub is fashioned as a trifurcated manifold 80. Those skilled in the art will appreciate that trifurcated manifold 80 is merely one example of a suitable hub, and other variations may be substituted. Proximal end 64 of elongated tubular body 62 is received in a suitably-sized channel in manifold 80 in conventional fashion. Manifold 80 may include conventional suture wings 81 if desired. Extension tubes 82, 83, 84 extend in the proximal direction from respective openings (not shown) in manifold 80. Each of extension tubes 82, 83, 84 communicates with a separate one of lumens 68, 69, 70. Typically, extension tubes 82, 83, 84 will comprise generally flexible polymers of a type commonly used for such purposes in the medical device art, such as polyurethane, PVC and silicone. In the non-limiting embodiments shown, one or more of extension tubes 82, 83, 84 may include a fitting 85 at the proximal end for engagement with a complementary fitting on an auxiliary device.

Fitting 85 of extension tube 82 may be connected to a source of an inflation fluid (not shown) for transmission of the inflation fluid through lumen 68 to the interior space of balloon 74 as before. The respective fittings on extension tubes 83, 84 may be connected, e.g., to fluid sources in the same manner as extension tube 34 in the embodiment of FIGS. 1-3.

Those skilled in the art will appreciate that elongated medical apparatus 10, 60 may be utilized in a plethora of different ways to gain access to body anatomy. For example, apparatus 10, 60 may be introduced into the vascular system to provide access to a target anatomical site for uses such as balloon angioplasty, stent delivery, or central venous fluid delivery. Apparatus 10, 60 may also be used to gain access to other target anatomical sites through other cavities and canals of the body, including but not limited to, the urinary tract, anal canal, and colon. Similarly, the inventive apparatus may be introduced as a conduit through the naso-gastric and/or naso-jejunal system for delivery and/or withdrawal of fluids, or for endoscopy. Other uses are contemplated, and are considered within the scope of the invention. In each instance, it is believed that the use of the elongated apparatus having an inflatable tip as described will reduce the risk of puncture and trauma when compared to the use of an elongated apparatus not provided with an inflatable tip.

FIG. 7 schematically depicts a method of using the inventive apparatus for gaining access to body anatomy. As illustrated therein, the step of providing the elongated medical apparatus 10, 60 is indicated at 100. Inflation of the distal tip 17, 45, 74 is indicated at 102. Insertion of the distal end 17, 46, 67 of the elongated tubular body 12, 42, 62 into a bodily passageway is indicated at 104. Advancing the distal end of the elongated tubular body to the targeted body anatomy is indicated at 106. Those skilled in the art will appreciate that the indication of steps 100, 102, 104, 106 as illustrated does not necessarily mean that such steps must be carried out in the sequence shown.

It is therefore intended that the foregoing detailed description be regarded as illustrative rather than limiting, and that it be understood that it is the following claims, including all equivalents, that are intended to define the spirit and scope of this invention.

The invention claimed is:

1. An elongated medical apparatus suitable for insertion into a bodily passageway of a patient for carrying out a medical procedure, comprising:

an elongated tubular body having an outer diameter, a proximal portion and a distal portion, said distal portion terminating at a distal end, said tubular body having a plurality of lumens extending therein, said plurality of lumens comprising a larger diameter lumen and a smaller diameter lumen, said larger diameter lumen closed at said tubular body distal end, and said smaller diameter lumen open at said distal end, said elongated tubular body including at least one side port along a length thereof, said side port positioned along said tubular body such that said larger diameter lumen communicates with an environment exterior of said apparatus through said side port;

and an inflatable member mounted to said distal end of said tubular body and extending distally therefrom, an interior space of said inflatable member in communication with said smaller diameter lumen for receiving an inflation fluid through said smaller diameter lumen distal end, said inflatable member having an outer diameter upon inflation that does not exceed the outer diameter of the tubular body.

2. The apparatus of claim 1,
wherein said apparatus is structured such that said inflatable member is inflated to said outer diameter for facilitating advancement of said apparatus in said bodily passageway.

3. The apparatus of claim 2, wherein said outer diameter of said inflatable member tapers to a smaller diameter distal tip.

4. The apparatus of claim 1, wherein said tubular body includes a third lumen extending therein.

5. The apparatus of claim 4, wherein said elongated tubular body includes at least one additional side port along a length thereof, said additional side port positioned along said tubular body proximal of said inflatable member such that said third lumen communicates with an environment exterior of said apparatus.

6. The apparatus of claim 1, further comprising a hub at a proximal end portion of said elongated tubular body, said hub structured for passage of respective fluid streams therethrough, each of said fluid streams communicating with a separate one of said lumens.

7. The apparatus of claim 1, wherein said inflatable member comprises a compliant composition.

8. The apparatus of claim 7, wherein said composition comprises polyurethane, silicone, polyethylene, PVC, or latex.

9. The apparatus of claim 1, wherein the inflatable member is formed from the same composition as the elongated tubular body.

10. The apparatus of claim 1, wherein said inflatable member is inflatable to a length of about 0.5 to 5 cm distal to the distal end of said elongated tubular body.

11. The apparatus of claim 10, wherein said inflatable member is inflatable to a length of about 1 cm beyond the distal end of said elongated tubular body.

12. The apparatus of claim 1, wherein said inflatable member is fixedly mounted to said tubular body distal end by one of adhesion and heat sealing.

13. The apparatus of claim 1, wherein said balloon comprises a compliant balloon comprising polyurethane, silicone, polyethylene, PVC, or latex, and wherein said balloon is substantially imperforate to prevent leakage of fluid therethrough.

* * * * *